United States Patent [19]
Tate

[11] Patent Number: 6,163,889
[45] Date of Patent: *Dec. 26, 2000

[54] ARTICLE OF CLOTHING WITH EMBEDDED MAGNET

[76] Inventor: John R. Tate, 11621 Markon Dr., Garden Grove, Calif. 92841

[*] Notice: This patent is subject to a terminal disclaimer.

[21] Appl. No.: 09/336,072

[22] Filed: Jun. 18, 1999

Related U.S. Application Data

[63] Continuation-in-part of application No. 09/187,684, Nov. 5, 1998, Pat. No. 5,996,116.

[51] Int. Cl.$^7$ ........................................................ A42B 1/24
[52] U.S. Cl. ............................................ 2/209.13; 2/195.1
[58] Field of Search ................................ 2/209.13, 175.1, 2/12, 195.1, 425

[56] References Cited

U.S. PATENT DOCUMENTS

| | | | |
|---|---|---|---|
| 459,942 | 9/1891 | Brown | 2/209.13 |
| 3,886,508 | 5/1975 | Lavard | 335/285 |
| 4,885,195 | 12/1989 | Change, III | 428/36.1 |
| 5,295,683 | 3/1994 | Tate . | |
| 5,305,999 | 4/1994 | Tate . | |
| 5,604,960 | 2/1997 | Good . | |
| 5,715,539 | 2/1998 | Benecki et al. | 2/160 |
| 5,740,557 | 4/1998 | Reid et al. | 2/209.13 |
| 5,898,943 | 5/1999 | Kim | 2/161.2 |
| 5,898,946 | 5/1999 | Keating et al. | 2/209.13 |
| 5,950,239 | 9/1999 | Lopez | 2/115 |
| 6,006,363 | 12/1999 | Karlin | 2/228 |

FOREIGN PATENT DOCUMENTS 2323018  3/1997  United Kingdom .

Primary Examiner—Bibhu Mohanty
Attorney, Agent, or Firm—Charles H. Thomas

[57] ABSTRACT

A golf ball marker or other small article that is attracted by the force of magnetism is carried in open display on a fabric article of clothing or other fabric accessory. The ferrous article remains in position on the clothing due to the force of magnetism. To produce this effect, a permanent magnet is secured in position on the fabric article, often in contact with a concealed side of a layer of fabric of which the fabric article is formed. A golf ball marker, golf divot repair tool, golf pencil with a ferrous band, or other article that is constructed of or which includes a ferrous material is placed into contact with an exposed layer of the fabric to which the permanent magnet is secured. The ball marker or other article is held by the force of magnetic attraction that typically acts through the fabric layer of material from the concealed side thereof to create a magnetic field on the visually exposed side of the fabric material. The ball marker or other material remains in position until purposefully dislodged by a force that opposes and overcomes the magnetic field created by the permanent magnetic. The permanent magnet may be incorporated into the crown, bill, or band of a hat or cap, a golf sun visor, or into the closure flap of a golfing glove, a golf towel, or the structure of a golf bag. The magnetic retention system may be sold as a unit for attachment to a layer of fabric. Such an embodiment may take the form of a tray formed of flexible plastic that defines a cavity that receives the magnet.

24 Claims, 8 Drawing Sheets

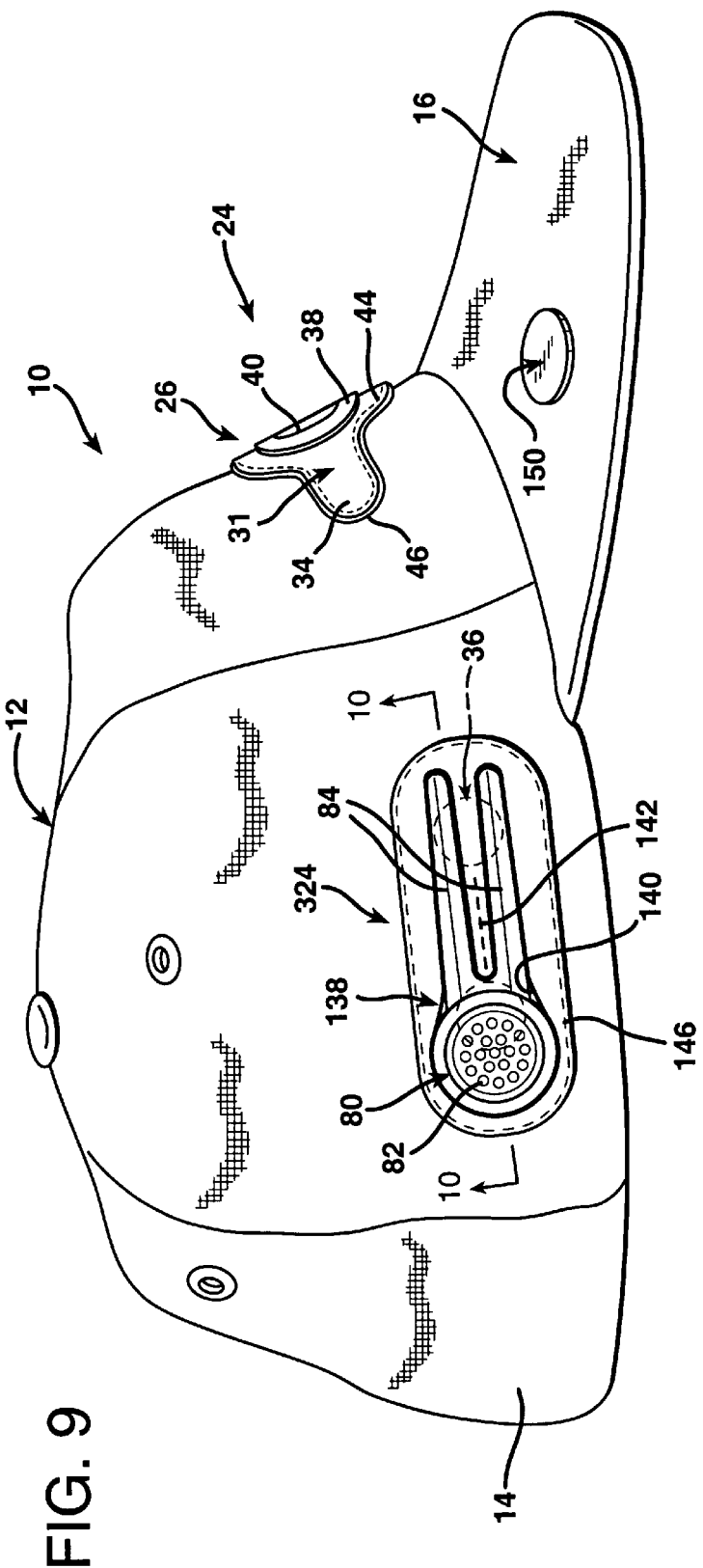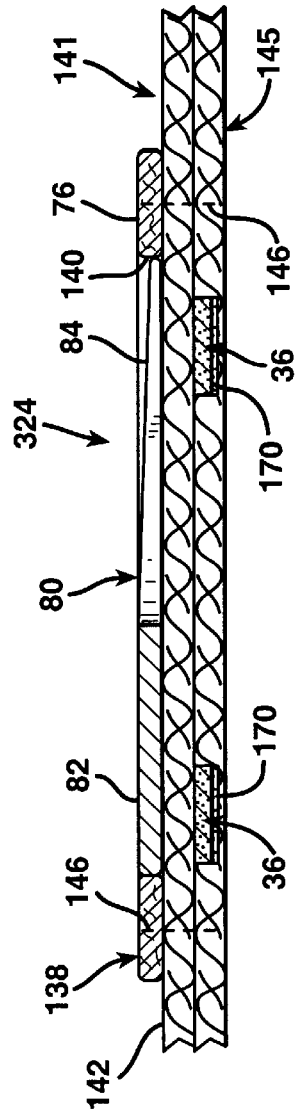
FIG. 9
FIG. 10

ARTICLE OF CLOTHING WITH EMBEDDED MAGNET

The present application is a continuation in part of U.S. application Ser. No. 09/187,684 now U.S. Pat. No. 5,996,116, filed Nov. 5, 1998, presently pending.

BACKGROUND OF THE INVENTION

1. Field of the Invention

The present invention relates to a system for releasably securing an article constructed of a material that is attracted by magnetism to an article formed of a fabric material, such as an article of clothing. The invention has particular applicability for use in releasably securing golf ball markers and golf divot repair tools to articles of clothing worn by golfers, and to other fabric articles utilized by golfers.

2. Description of the Prior Art

Golf ball markers have been used for many, many years in order to mark the position of a golf ball on a fairway or green during a game of golf engaged in by competitive players. Golf ball markers are typically formed as small, disc-shaped structures, usually fabricated from metal. Conventional golf ball markers are often stamped from a ferrous material, usually steel or iron. Some conventional golf ball markers have a plain, unadorned appearance, although in more competitive golfing circles ball markers having surface embellishments on their faces are now widely utilized. Conventional ball markers may include the sculptured and/or painted reproductions of a golf course or tournament logo, a country club insignia, a corporate or university logo or insignia, or more personalized surface embellishments. Whatever the particular adornment adopted for a golf ball marker by a player, more often than not the player is proud to display the ball marker, since it is frequently indicative of courses or tournaments in which the player has participated or otherwise attests to the players experience or competence in participation in the game of golf.

While a player may be happy to display a ball marker, in conventional use golf ball markers offer only a limited opportunity for such display. More often, when a golfer's ball lies in the field of play, the ball marker is typically carried in the golfer's pocket, and is thus concealed from view. Furthermore, when a golf ball marker is carried in a player's pocket, the player is often forced to dig and fumble through the contents of the pocket in order to retrieve it. Golf ball markers have similar sizes and shapes to coins of currency, which are often carried in the same pocket. A golf ball marker therefore cannot be separated easily from the other contents of the pocket by the sense of touch. The retrieval of a golf ball marker for use in this way thereby creates a source of annoyance and distraction to the golfer.

Systems for enhancing the convenience of access and extent of display of golf ball markers have been devised in the past. For example, golf ball markers may be releasably mounted by means of magnets in golf divot repair tools that are utilized to repair divots and spruce up golf greens. Golf divot repair tools may be formed with one or more shallow, disc-shaped recesses therein at the bottom of which a flat slab of magnetic material is permanently secured. A ferrous ball marker formed of steel or soft iron may then be releasably held in position in the recess or tray of a golf divot tool by the magnetic force of attraction of the magnetic material. As a consequence, when the divot repair tool is utilized the ball marker is conveniently accessible and is also displayed for all to see.

U.S. Pat. Nos. 5,295,683 and 5,305,999 disclose and describe divot tools of different configurations in which golf ball markers are releasably mounted by the force of magnetic attraction. Also, the tool of U.S. Pat. No. 5,305,999 includes a clip that may be attached to the belt, cap, shoe, pocket, or golf bag of a golfer. As a consequence, when the divot tool is carried in this manner the golf ball marker is more easily retrieved and is also prominently displayed. Nevertheless, since divot repair tools themselves are used only on limited occasions, the opportunities for conveniently retrieving a golf ball marker by releasably mounting it on a divot repair tool are somewhat limited.

SUMMARY OF THE INVENTION

The present invention involves a system in which a golf ball marker, a golf divot tool, or some other small, light-weight article utilized in sports or in recreation is retained in a very convenient and accessible location. Moreover, the light-weight iron or steel article is held in a position releasably secured to a cloth article upon which it is prominently displayed and exposed. The retention system of the invention involves releasably positioning a light-weight, magnetically attractable article on the exposed fabric surface of a user's clothing or upon other fabric accessories to which a permanent magnet has been securely attached. For example, golf ball markers may be prominently displayed on golf hats, caps, sun visors, golfing gloves, golf towels, golf bags, shirts, jackets, umbrellas, and other golfing accessories formed of fabric.

The system of the invention is not limited to the field of golf, but can be utilized in other field as well. For example, the system of the invention is quite useful in fly fishing in order to hold an artificial casting fly with a hook incorporated therein on the hat of a person engaged in fly fishing.

The system of the invention for retaining small, magnetically attractable articles in position on an article of clothing or other fabric involves the incorporation of a flat strip or slab of magnetic material or a plurality of flat magnetic discs or other permanent magnets into the fabric structure of an article of clothing or some other fabric accessory. According to the invention, a magnet is mounted on or beneath the exposed surface of the fabric of an article of golf wear or a fabric article of wear utilized in some other sporting or recreational pursuit. The magnet is a permanent magnet and is secured out of sight. This may be accomplished by securing the magnet on the concealed side of a fabric article of clothing by use of an adhesive, or otherwise. The force of magnetic attraction acts through the fabric material with sufficient strength so that a ferrous golf ball marker or other small iron or steel sporting or recreational article is held in position against the visually exposed surface of the fabric while the magnet exerting the magnetic field remains concealed from view on the inside, hidden surface of the fabric.

Alternatively, the magnet may be mounted in a holder or frame that defines a shallow cavity shaped to conform to the shape of a small iron or steel article. The holder or frame forms a shallow pocket or cavity into which the ball marker or other small ferrous article snugly fits. The ball marker or other article conceals the magnet from view when it is located in the frame cavity that is attached to the outer surface of the fabric article.

By utilizing the system of the invention, ball markers, divot tools, and other small articles constructed of materials that are attracted by magnetism will adhere to articles of clothing and can be held in place of the force of magnetic attraction with sufficient strength so that they will not become dislodged therefrom accidentally. To the contrary, the magnetic field exerted by the magnet, even if it is through the fabric structure of the article of clothing, is sufficient to hold a ferrous ball marker or other small article in position until and unless the user purposefully overcomes that force and pulls the ferrous article clear of the magnetic field of attraction. This force may be applied by the thumb and forefinger of the user's hand to remove the ball marker or other article from the fabric layer.

In one broad aspect, the invention may me considered to be an improvement in an article of clothing with at least one layer of fabric having a visually exposed side and an opposite concealed side. The improvement of the invention is comprised of a permanent magnet secured in position to the layer of fabric at a selected, fixed location thereon to exert a magnetic field from the selected fixed location at the visually exposed side of the layer of fabric.

The term fabric, as used herein, is to be construed in its broadest sense of any thin, expansive, flexible, or supple material of the type utilized in the construction of clothing, as well as other in the construction of sporting and recreational accessories, such as bags, towels, flags, etc. The term fabric should be construed as encompassing not only woven cloth textiles, but also other flexible, thin, expansive materials such as nylon, leather, plastic sheet material, and felt, for example.

In one preferred embodiment of the invention, the improved article of clothing is a hat that has a bill formed with a stiff, substantially flat interior core. The core of the bill is encapsulated within a cloth fabric that covers both sides of the core. The permanent magnet may be glued or otherwise held in position within an opening defined through the structure of the flat, stiff core material of the bill of the cap. The magnet is covered by overlying fabric layers on both sides of the core.

The permanent magnet is preferably formed of a small annular ring or disc of iron which has been permanently magnetized. The permanent magnet may also be formed of a small disc cut from a flexible sheet or layer of rubber with magnetized ferrous particles of iron or iron oxide embedded therein and which have been permanently magnetized. Alternatively, the permanent magnet may be comprised of one or more thin, magnetic slabs, formed as discs, rectangles, or any other geometric shape. In still another alternative arrangement the magnetic material may be formed as lengths of magnetic wire. Magnetic material having other physical shapes may also be utilized.

In a preferred embodiment of the invention the permanent magnet is formed as a thin, flat, annular ring of iron which has been permanently magnetized. The use of a permanent magnet in the shape of an annular ring has several advantages, which will be described in association with various embodiments of the invention.

In another aspect, the present invention may be considered to be an improvement in an article of clothing formed of flexible, fabric material. The improvement of the invention includes a shallow tray having a floor, walls projecting outwardly from the floor to define a laterally enclosing cavity, and a rim extending laterally beyond the walls and having an outwardly facing attachment surface surrounding the cavity. A layer of adhesive is interposed between the attachment surface of the rim and one surface of the fabric material, thereby joining the tray to the fabric material with a hollow cavity enclosed therebetween. A permanent magnet is disposed in the cavity. The magnet exerts a magnetic force of attraction through the fabric material and beyond so that a magnetic field of attraction exists on the side of the material opposite the side thereof at which the layer of adhesive joins the tray to the fabric material.

The foregoing embodiment of the invention involves an apparatus or device in the form of a generally flat patch that may be attached to the inside, concealed surface of an article of clothing or other fabric structure. Prior to attachment the apparatus is provided with a film coated with a release agent that covers the layer of adhesive. When the patch is to be applied to the inside or concealed surface of the article of clothing the release film is stripped from the adhesive layer and the adhesive layer is pressed against the surface of the fabric on the concealed side thereof. The magnet is thereby securely attached to the layer of fabric so as to exert a magnetic force of attraction through it which acts on the opposite, visually exposed side of the fabric. When a ferrous golf ball marker or other small article that is attracted by magnetic force is brought into the influence of the magnetic field, it will be drawn into contact with the visually exposed surface of the fabric and held against that outer surface until purposefully removed.

In still another aspect the invention may be considered to be an apparatus securing a magnet to clothing to attract a ball marker. The apparatus of the invention is comprised of a shallow tray having a floor, walls projecting outwardly from the floor to define a laterally enclosed cavity, and a rim extending laterally beyond the walls and having an outwardly facing attachment surface surrounding the cavity. A permanent magnet is disposed in the cavity of the tray. A layer of adhesive on the attachment surface is provided for establishing an adhesive bond with fabric placed in contact therewith. When that adhesive bond is established, the magnet is encapsulated between the tray and the fabric.

The invention may be described with greater clarity and particularity by reference to the accompanying drawings.

DESCRIPTION OF THE DRAWINGS

FIG. 9 is a side elevational view illustrating still another alternative embodiment of the invention as incorporated into the hat of FIG. 1.

FIG. 10 is a sectional detail of the embodiment of FIG. 9 taken along the lines 10—10 thereof.

DESCRIPTION OF THE EMBODIMENTS

Figure 1:
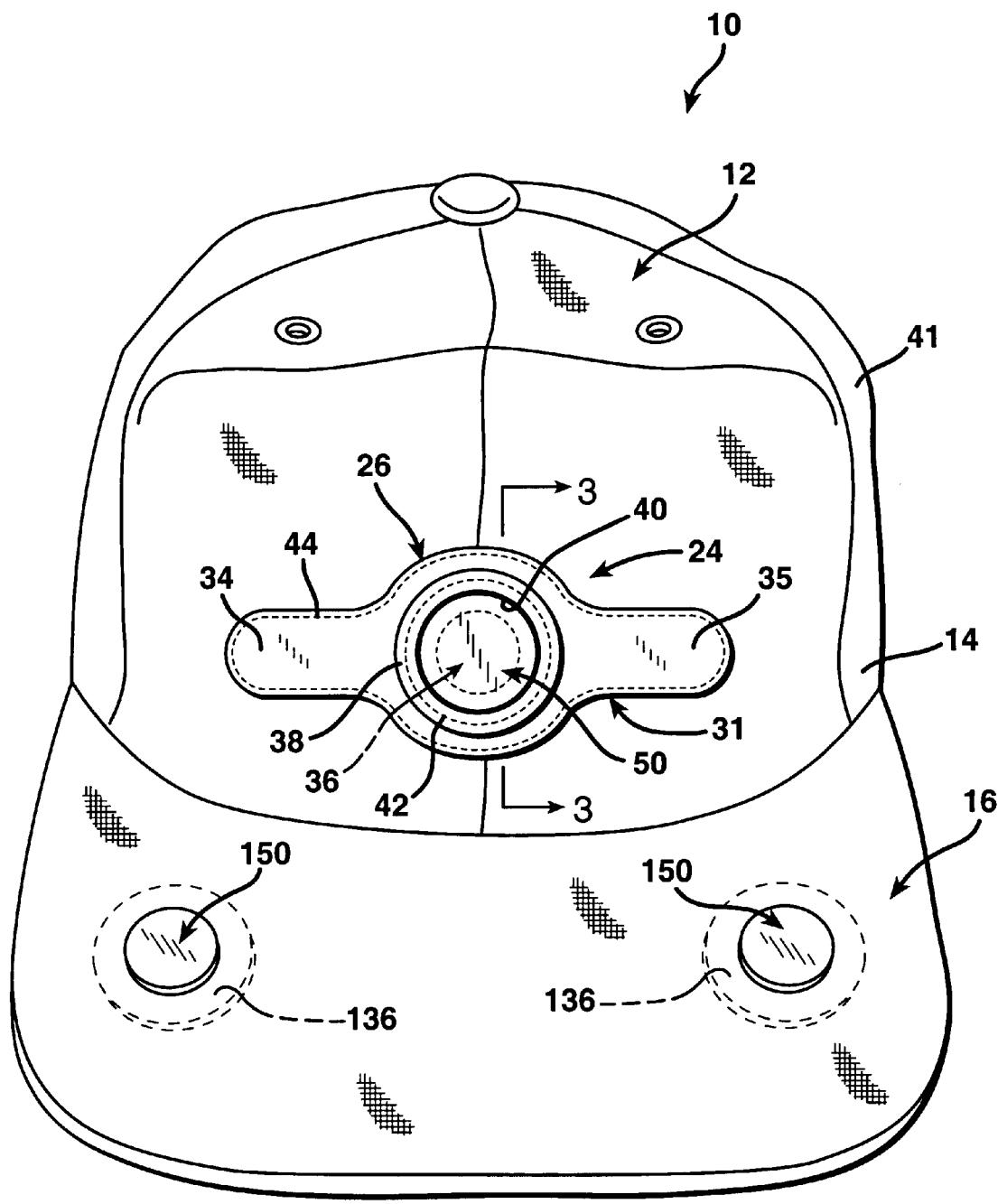
FIG. 1 is a front, perspective view of a fabric cap or hat with the improvement according to the invention.

FIG. 1 illustrates a fabric golf hat or cap indicated generally at 10. The cap 10 is formed with a cotton, wool, or synthetic fabric layer 41 forming a crown 12 surrounded by a hatband 14 at its lower extremity. In the forehead region a bill 16 is secured to the hatband 14. The bill 16 is constructed with a generally flat core 18, visible in the broken away view of FIG. 4, which may be formed of fiberboard or some other material stiff enough to provide the bill 16 with a permanent shape. The flat, roughly crescent-shaped core 18 is wrapped above and below within a sheet of fabric that forms a layer 20 on the underside of the bill 16 and an overlying fabric layer 22 that forms the upper, exposed surface of the bill 16, as illustrated in the sectional view of FIG. 5.

Figure 2:
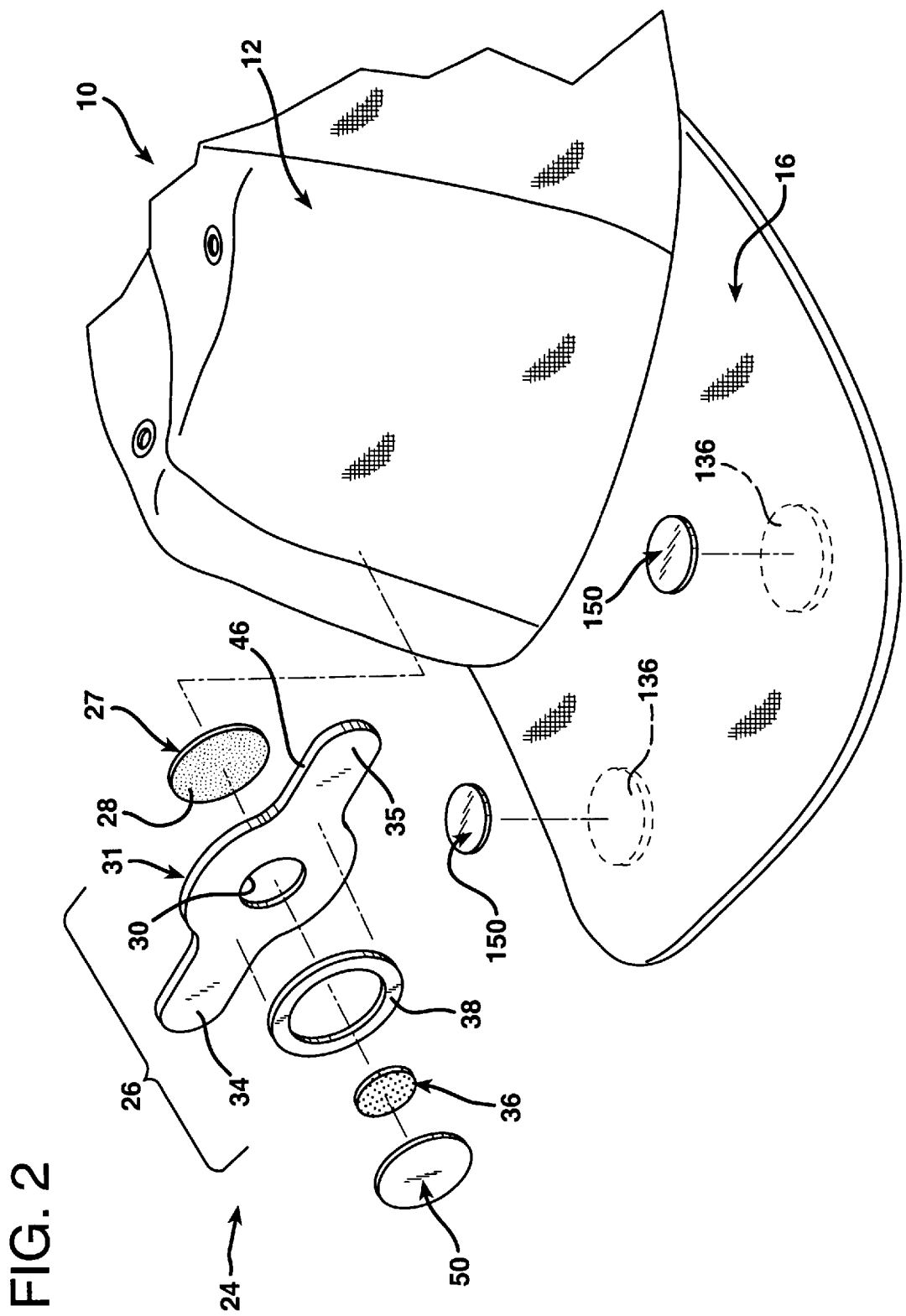
FIG. 2 is an exploded perspective view illustrating the improved article of clothing of FIG. 1.
Figure 3:
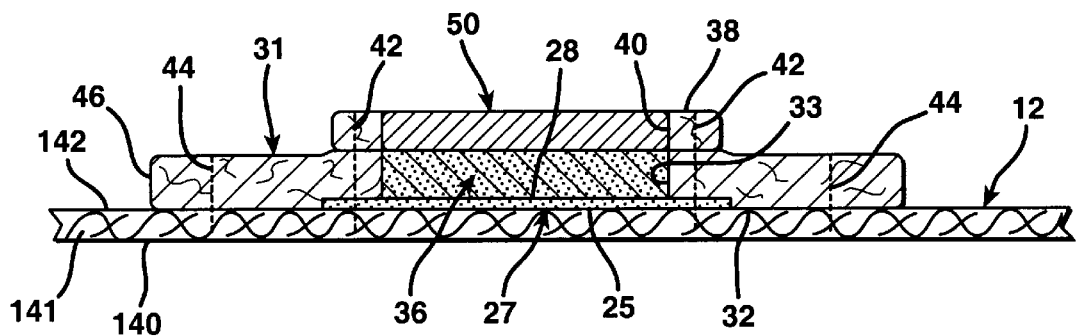
FIG. 3 is a cross-sectional view of the embodiment of the accessory of the invention that is secured to the forehead area of the crown of the cap taken along the limes 3—3 of FIG. 1.

The golf hat 10 incorporates several different embodiments of the present invention. As illustrated in FIGS. 2 and 3, the golf hat 10 includes an assembly 24 that is comprised of a shallow tray 26. A portion of the tray 26 is formed as a flat structure die cut from flat sheet material and having a relatively large, generally annular central region with a pair of laterally projecting wings 34 and 35 extending therefrom. The tray 26 has a floor that is formed by a flat, disc-shaped adhesive patch 27 that is faced on both of its flat, expansive faces 25 and 28 with adhesive. The face 28 of the patch 27 forms the floor surface of the tray 26.

The tray 26 also includes walls 30 formed about the inner periphery of a central, disc-shaped opening through the central region of the flat sheet material of the tray 26. The structure of the flat sheet of material of the tray 24 that surrounds the central opening 30 therethrough serves as a rim 31 that includes the wings 34 and 35. The rim 31 extends laterally beyond the walls 30 to surround the cavity formed by the facing floor surface 28 of the patch 27 and the walls 30. The rim 31 has a flat, expansive attachment surface 32 that lies opposite the patch 27.

The apparatus 24 also includes a permanently magnetized iron or steel disc 36, which is secured in position within the cavity formed by the walls 30 and the facing floor surface 28 of the patch 27 by the adhesive on the floor surface 28 of the patch 27. The attachment surface 32 of the rim 31 is secured to the layer 41 of fabric crown 12 of the hat 10. The adhesive on the floor surface 28 of the patch 27 holds the magnet 36 at a selected, fixed location on the crown 12 of the hat 10. This selected, fixed location is in the forehead area of the crown 12 above the hatband 14 and centered with respect to the bill 16.

In the embodiment of FIGS. 2 and 3, the rim 31 of the tray 26 is formed of a flat sheet of flexible stock, which may, for example, be die cut from a sheet of leather. The walls 30 of the cavity 33 are defined as the sides of a die cut opening through the flat sheet of leather stock. As illustrated in FIGS. 2 and 3, the floor surface 28 is covered with an adhesive to hold the magnet 36 secured in the tray 26 and against the floor surface 28. The patch 27 has a peripheral margin that extends laterally beyond the opening in the sheet of leather stock forming the rim 31. This peripheral margin is captured between the attachment surface 32 of the rim 31 and the fixed, central forehead location on the visually exposed side 42 of the layer 41 of fabric forming the crown 12 of the cap 10.

The tray 26 is further comprised of a flat, annular ball marker retaining ring 38 that is disposed in contact with the rim 31 of the tray 26 opposite the attachment surface 32 thereof. The retaining ring 38 surmounts the rim 31 with the patch 27 centered therebeneath as illustrated in FIG. 3. The retaining ring 38 thereby defines a laterally constraining disc-shaped enclosure 40 suitable for receiving a golf ball marker 50.

The magnet 36 is secured in the cavity 33 by the adhesive coating on the outwardly facing surface of the adhesive patch 27. The adhesive bond created between the patch 27 and the magnet 36 is significantly stronger than the force of the magnetic field created within the enclosure 40. The tray 26 is secured to the front of the fabric crown 12 by two lines of stitching, indicated at 42 and 44, respectively, in FIG. 3. The line of stitching 42 is formed by thread stitched in a circular pattern about the enclosure 40. The line of stitching 42 extends through the retaining ring 38, through the rim 31, through the periphery of the circular, double-faced adhesive tape patch 27, and through the fabric of the hat 10 forming the crown 12. The second line of stitching 44 is about the periphery of the rim 31. The line of stitching 44 extends through the structure of the rim 41 and through the fabric forming the crown 12 of the hat 10 about the periphery of the rim 31, spaced just inwardly from the peripheral edge 46 of the rim 31.

While the adhesive on the patch 27 is normally strong enough by itself to hold the magnet 36 firmly and permanently attached to the hat 10 in the cavity 33 formed within the rim 31, the magnet 36 can be held in place by other constraints. For example, the central, circular opening in the ring 38 may be formed with a diameter slightly smaller than the diameter of the opening through the rim 31 forming the cavity 33. In such a construction, the structure of the ring 38 will overhang and reside radially inwardly from the walls 30 of the cavity 33 formed in the rim 31. This overhang can form a restraining ledge that captures the peripheral margin of the magnet 36 and holds it in the cavity 33.

The whole purpose of providing the hat 10 with the tray 26 is to provide a seat and a way of magnetically attaching a ferrous article, such as the golf ball marker 50 to the hat 10. The ball marker 50 is formed as a flat disc of iron or steel, typically painted or otherwise decorated on one side. The steel ball marker 50 seats snugly within the confines of the enclosure 40 formed within the retaining ring 38.

A golfer is thus provided with a system for conveniently and releasably attaching the ball marker 50 to an article of clothing, such as the hat 10. The golfer will normally carry the ball marker 50 placed in the enclosure 40 at the front of the crown 12 of the hat 10. When the ball marker 50 is required to spot the position of a golf ball, the golfer merely extracts the golf ball marker 50 from the retaining ring 38 by merely flexing the structure of the tray 26 at the peripheral edge of the retaining ring 38. The golfer then seizes the ball marker 50 between thumb and forefinger and withdraws it from the retaining ring 38, thereby overcoming the magnetic force of attraction exerted by the magnet 36. The golfer then places the ball marker 50 on the field of play where appropriate. The ball marker 50 is stored by merely lifting it from the field of play and placing it in alignment with the center of the retaining ring 38 in close proximity thereto. The magnetic force of attraction of the magnet 36 thereupon draws the ball marker 50 into the encircling enclosure 40 and holds it at the front of the hat 10.

The releasable attachment system of the invention does not necessarily require a tray to secure a magnet to an article of clothing. As illustrated in FIGS. 1–5, a generally disc-shaped magnet 136 may be secured to the hat 12 in a different manner. As illustrated in drawing FIGS. 4 and 5, the stiff core 18 of the hat bill 16 may be formed with one or more generally disc-shaped openings 133 therein. As previously described, the hat bill 18 is constructed with lower and upper fabric layers 20 and 22, respectively, that reside beneath and atop the stiffer core 18. Therefore, if a disc-shaped magnet 136 is installed in the opening 133 in the core 18 before the fabric layers 20 and 22 are permanently secured to hatband 14, the magnet 136 will be encapsulated in the cavity defined by the disc-shaped opening 133 in the core 18 and the fabric layers 20 and 22 below and above the core 18.

The fabric layers 20 and 22 are each only a fraction of an inch in thickness so that their presence does not materially attenuate the force of magnetic attraction exerted by the magnet 136 at either the exposed upper surface of the fabric layer 22, or the undersurface of the cap bill 16 either, for that matter. As a consequence, a significant magnetic force is exerted through both the fabric layers 20 and 22, both of which lie in direct contact with the magnet 136.

As illustrated in FIG. 1, a small, disc-shaped golf ball marker 150, formed of a ferrous material such as steel or soft iron, can be placed atop the fabric layer 22 and will be held secured in place on the upper, exterior surface of the fabric layer 22 until purposefully removed by a force that overcomes the force of magnetic attraction of the magnet 136. The ball marker 150 will be held in position regardless of the orientation of the hat 10. That is, the hat 10 may be removed from the head of the golfer, turned upside down, and otherwise manipulated without dislodging the ball marker 150 from the exposed surface of the fabric layer 22.

Figure 4:
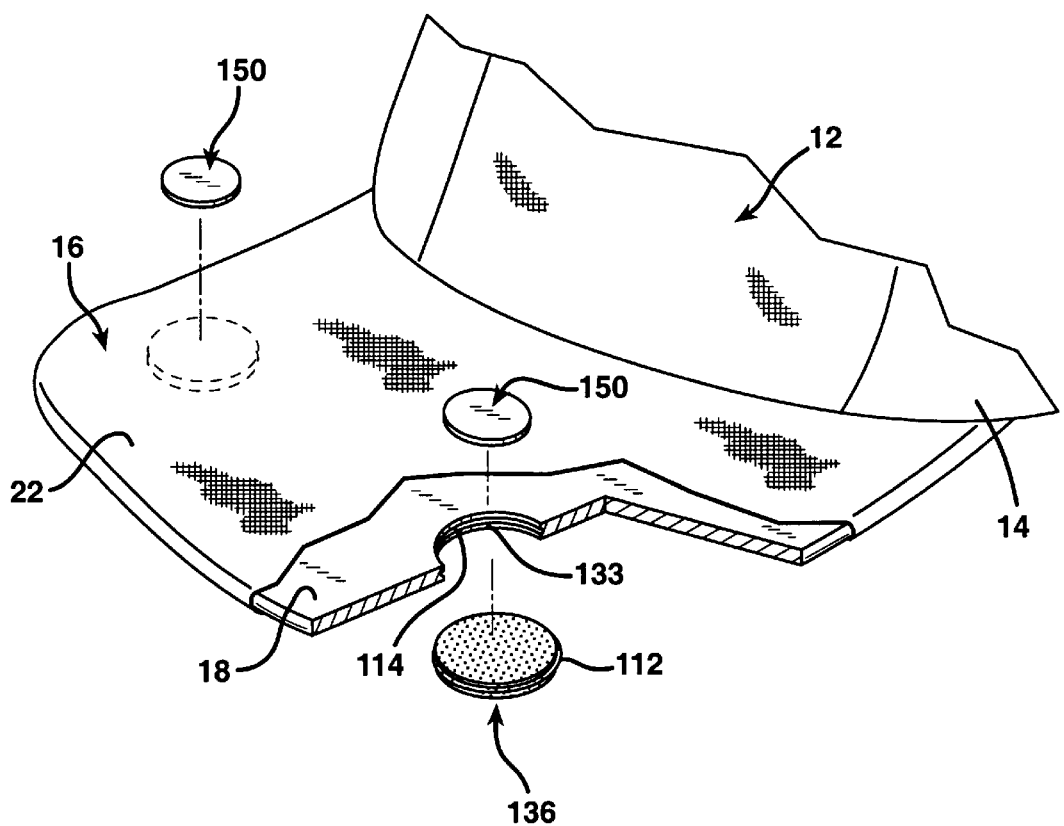
FIG. 4 is an exploded, perspective view, partially broken away, illustrating one alternative embodiment of the invention as incorporated in the same hat of FIGS. 1 and 2.
Figure 5:
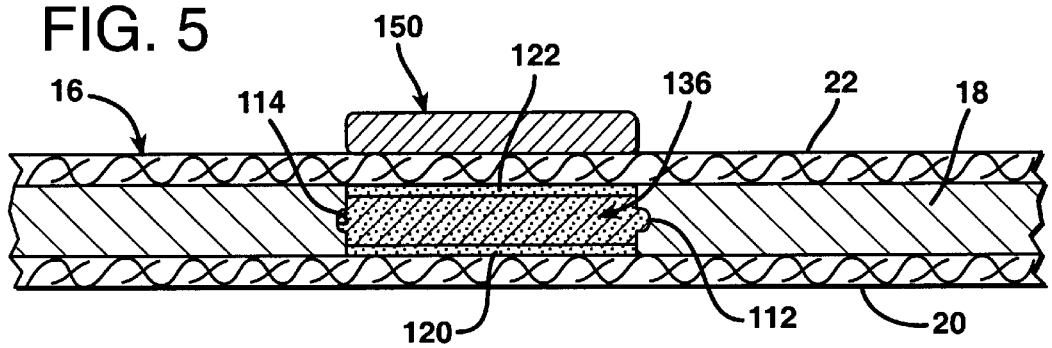
FIG. 5 is a sectional elevational detail illustrating the embodiment of the invention depicted in FIG. 4.

It may be desirable to provide some system to aid in immobilizing the magnet 136 in the cavity formed by the hole 133 in the hat bill core 18. As illustrated in FIGS. 4 and 5, the magnet 136 may be formed with a radially outwardly projecting rib 112. The annular rib 112 is formed as a narrow, radially outwardly projecting protrusion that extends about the entire periphery of the magnet 136. Also, the hole 133 defined through the core material 18 may be formed with a laterally projecting annular groove 114. The groove 114 is defined in the stiffening material 18 of the bill 16 about the entire circumference of the hole 133 therein.

The structure of the stiffening material 18 is sufficiently resilient so that the magnet 136 can be forced into the opening 133 until the rib 112 is aligned with the groove 114. The groove 114 thereupon receives the rib 112 so that the magnet 136 is securely lodged within the structure of the bill core 18 and does not tend to pull outwardly therefrom when the ball marker 150 is removed from the fabric layer 22 of the cap bill 16.

Figure 6:
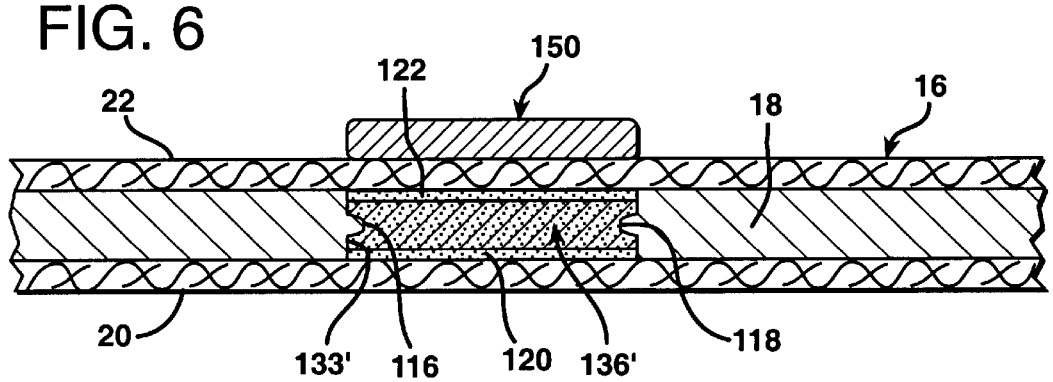
FIG. 6 is a sectional elevational detail illustrating an alternative embodiment of the invention to that depicted in FIGS. 4 and 5.

FIG. 6 illustrates an equivalent detent arrangement as an alternative system of lodging the magnet 136' in the stiffening core 18 of the cap bill 16. Specifically, in the embodiment of FIG. 6 the opening 133' defined through the bill core 18 is formed with a radially projecting rib 116 that extends laterally and radially inwardly from the inside of the opening 133' in the stiffening core layer 18. The magnet 136' has a generally disc-shaped configuration, but with a laterally projecting groove 118 defined in its periphery. The groove 118 in the magnet 136' receives the rib 116 formed about the inner circumference of the opening 133'. The interaction between the rib 116 and the groove 118 likewise aids in immobilizing the magnet 136' in the cavity formed in the bill 116, even when the ball marker 150 is pulled away from the magnetic field exerted by the magnet 136' in the cap bill 16.

In both of the embodiments of FIGS. 5 and 6, a further aid in maintaining the magnet in position within the core 18 of the cap bill 16 is provided by coating the upper and lower circular faces of the magnets 136 and 136' with layers of adhesive 120 and 122. These adhesive layers 120 and 122 form adhesive bonds between the magnets 136 and 136' and the surfaces of the fabric layers 20 and 22 which they contact.

Figure 7:
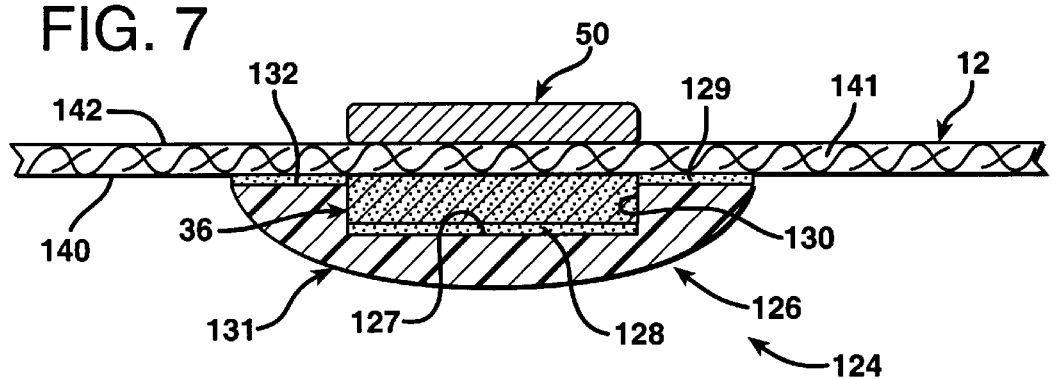
FIG. 7 is a sectional elevational detail illustrating a further alternative embodiment of the invention to that depicted in FIGS. 4 and 5.
Figure 8:
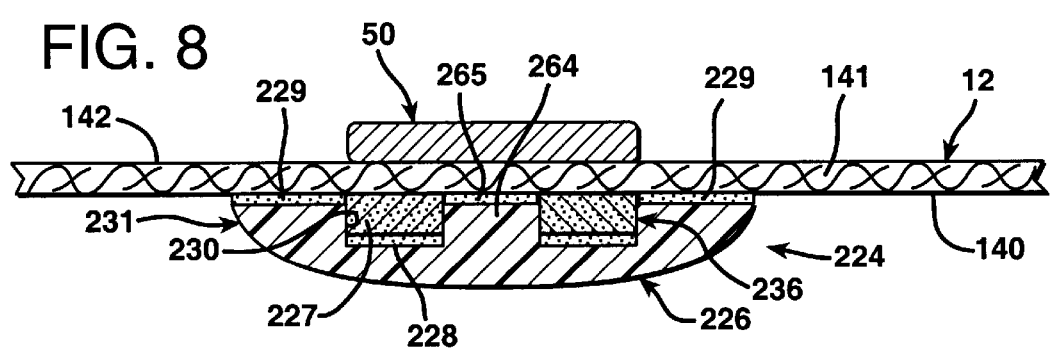
FIG. 8 is a sectional elevational detail illustrating still another alternative embodiment of the invention to that depicted in FIG. 7.

FIGS. 7 and 8 illustrate still another embodiment of the invention. In this embodiment a magnetic attachment device 124 includes a shallow tray 126 which is formed of a patch of flexible material. This material may be some type of flexible plastic, such as polyvinyl chloride, polyurethane, or polyethylene. The plastic tray 126 defines a tray cavity having a circular floor 127, cylindrical walls 130 projecting outwardly from the floor 127, and a rim 131 extending laterally beyond the walls 130. The rim 131 has an outwardly facing attachment surface 132 surrounding the disc-shaped cavity formed by the floor 127 and walls 130. The attachment surface 132 of the rim 131 is secured to the concealed side 140 of the layer of fabric forming the crown 12 of the hat 10 by a layer of adhesive 129. The disc-shaped permanent magnet 36 is thereby encapsulated between the tray 126 and the concealed side 140 of the fabric layer forming the crown 12 of the hat 10. The magnetic attachment device 124 may, for example, be attached to the inside of the crown 12 at the forehead area thereof in place of the apparatus 24 illustrated in FIGS. 1–3.

An adhesive layer 129 is applied over the attachment surface 132 of the tray rim 131 surrounding the cavity for the magnet, so that the plastic tray structure 126 may be pressed against and adhesively secured to a layer 141 of fabric material. The magnet 36 within the tray 126 easily exerts a sufficient magnetic force through the structure of the fabric 141 to attract a small iron or steel article against the visually exposed, opposite surface 142 of the fabric. The layer of adhesive 128 on the floor 127 of the tray 126 aids in holding the magnet 36 within the confines of the tray 126.

Prevention of premature contact of the adhesive layer 129 with another surface is achieved by covering the adhesive layer 129 with a conventional protective film coated with a release agent prior to application of the tray 126 to the crown 12 of the hat 10. To install the tray 126 as depicted in FIG. 7, the release-coated film is removed and the adhesive layer 129 is pressed against the concealed surface 140 of the inside surface of the fabric crown 12 of the hat 10. Due to its pressure-sensitive nature the annular adhesive layer 129 firmly secures the tray 126 in position on the inside of the hat 10.

The magnet 36 will attract the ball marker 50 as shown in FIG. 7 in the manner previously described. That is, when the ball marker 50 is moved into the vicinity of the location on the crown 12 behind which the concealed tray 126 is installed, the magnetic force of attraction of the magnet 36 acts through the fabric layer 141 of the crown 12 and holds the ball marker 50 flat against the visually observable surface 142 of the fabric layer 141 forming the hat crown 12. The ball marker 50 may thereupon be plucked from and returned to the surface of the crown 12 of the hat 10 without any means of location thereon or attachment thereto, other than the magnetic system of the invention.

It should be noted that in the embodiment of FIG. 7 there is no retaining ring, as in the embodiment of FIGS. 2 and 3. As a consequence, it has been found that sometimes the ball marker 50 will be attracted to the magnet 36, but will be held off center with respect to the magnet 36. This occurs because it is attracted to one or the other of poles of the permanent magnet 36.

To achieve generally coaxial alignment between the magnet and ball marker 50 without a retaining ring, the magnet may be formed as a flat, annular magnetized ring indicated at 236 in FIG. 8. In this arrangement the magnetic attachment device 224 has a tray 226 that is also formed of a flexible plastic material. However, the floor 227 of the cavity defined therein has an annular shape with a center post 264 centrally located within the tray cavity and extending upwardly to a level even with the tray walls 230. The magnet 236 is also formed with an annular, disc-shaped configuration, so that it has the shape of an annular ring. A flat, lower annular layer of adhesive 228 bonds the ring magnet 236 to the floor 227 of the tray 226.

An annular layer 229 of adhesive on the attachment surface of the rim 231 of the tray 226, together with a circular layer of adhesive 265 at the top of the mounting post 264, secure the tray 226 to the crown 12 of the hat 10. Specifically, the layers of adhesive 229 and 265 adhesively bond the tray 226 to the concealed side 140 of the fabric structure forming the hat crown 12. When an iron or steel ball marker 50 is brought into proximity to the position at the visually observable surface 142 beneath which the tray 226 is installed, the ring magnet 236 will exert a magnetic force of attraction through the fabric layer 141 forming the crown 12 of the hat 10. Because the magnet 236 has a ring-shaped construction, the magnetic force of attraction serves to center the ball marker 50 at the location of the magnetic attachment device 224 on the exposed surface 142 of the fabric layer 141 forming the hat crown 12, so that it is very nearly coaxially aligned with the ring magnet 236.

FIGS. 9 and 10 illustrate still another embodiment of the invention in which a magnetic attachment system 324 is utilized at a selected location on the hatband 14 of the hat 10. In the embodiment of FIGS. 9 and 10, two separate disc-shaped magnets 36 are interposed between the outer fabric layer 141 which extends upwardly to form the crown 12 of the hat 10 and an inner fabric layer 145 that is folded back under the lower edge of the hat 10 to form the inner layer of the hatband 14. The magnets 36 are secured to the fabric layer 145 by means of adhesive layers 170 that bond one of the faces of each of the magnets 36 to the inside layer 145 of the hatband 14.

On the outer, visually exposed surface 142 of the fabric layer 141 a retaining frame 138 is formed. The retaining frame 138 is a flat positioning frame that may, for example, be die cut from a sheet of leather stock. The frame 138 is secured to the outside layer 141 of the hat 10 on the visually exposed surface 142 thereof. The flat, positioning frame 138 has a border area 176 surrounding an opening 140 therein. The opening 140 extends entirely through the structure of the sheet material forming the frame 138 and has a shape configured to receive and snugly laterally surround an article attracted by magnetism.

In this embodiment of the invention the article to be held to the hatband 14 of the hat 10 by means of the magnetic retention system 324 is a steel divot repair tool 80. The divot repair tool 80 has a disc-shaped body 82 with a pair of elongated legs 84 extending therefrom. The divot repair tool 80 is of the type commonly utilized to spruce up greens and playing surfaces which may be marred slightly by golf shots.

The opening 140 within the frame 138 defines the selected, fixed location on the fabric layer 141 at which the magnetically attractable divot tool 80 is positioned in order for it to be retained on the hatband 14 by the magnets 36. The magnetic force of attraction of the magnets 36 acts through the structure of the fabric layer 141 to create magnetic fields at the visually exposed surface 142 thereof. One of the magnets 36 exerts a magnetic field at the end of the frame 138 that seats the disc-shaped body 82 of the divot tool 80, while the other magnet 36 exerts a magnetic force of attraction that attracts the legs 84 of the divot tool 80. As with the ball markers, the divot tool 80, when placed in the enclosure or cavity 140, is releasably secured to the hat 10 by a magnetic force of attraction of the magnets 36.

The divot repair tool 80 may be easily removed from the magnetic retention system 324 by gripping it with thumb and forefinger and lifting it out of the frame 138. The permanent magnets 36 are retained in position by the adhesive layers 170 that secure them to the fabric layer 145 of the hatband 114. Also, the frame 138 is retained in position by stitching 146 that extends about the periphery of the frame 138 and passes through the structure of both the frame 138 and both layers 141 and 145 of the hatband 14. A line of stitching 142 also extends through the frame 138 and layers 141 and 145 in at least a portion of the frame 138 that extends up between the legs 84 of the divot repair tool 80.

Figure 9A:
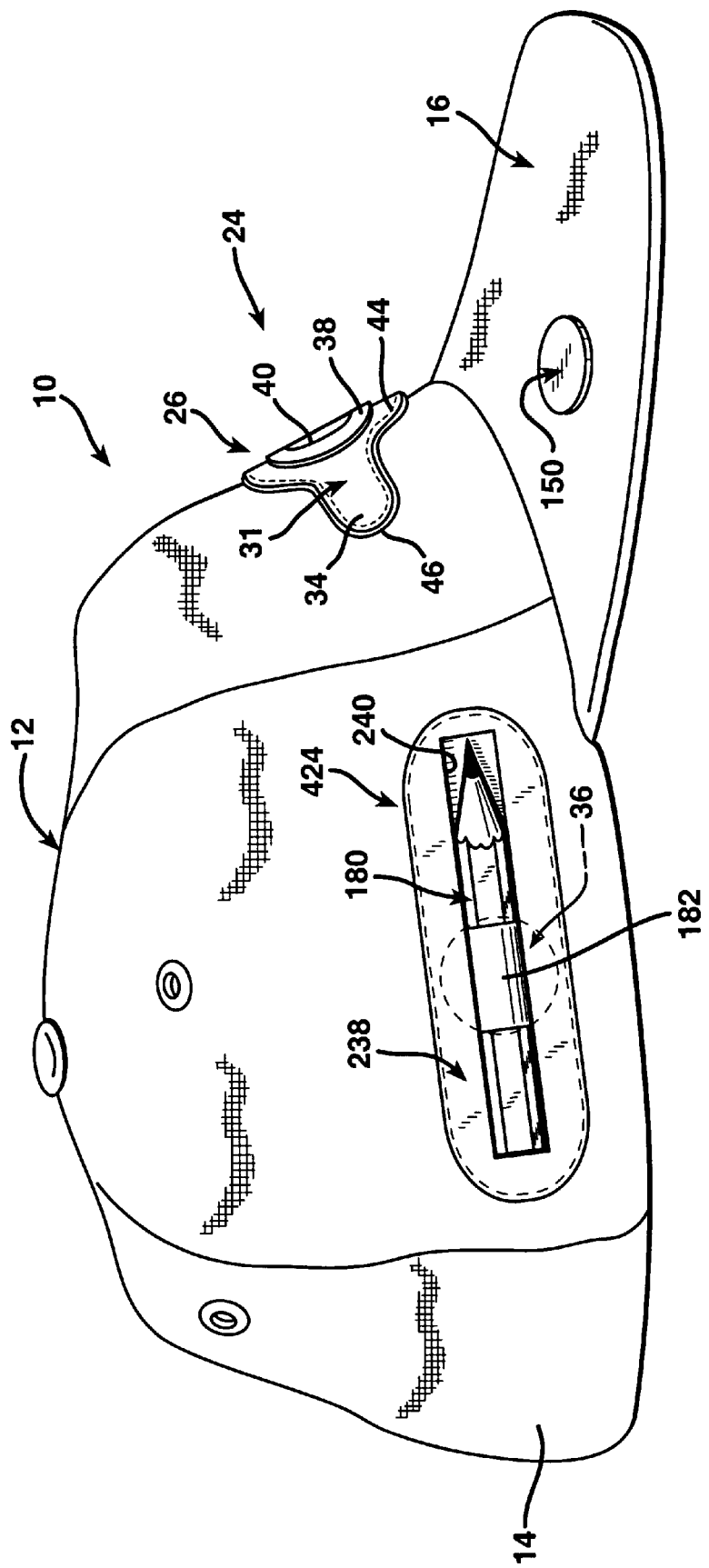
FIG. 9A is a side elevational view illustrating still another alternative embodiment of the invention as incorporated into the hat of FIG. 1.

FIG. 9A illustrates a modification of the magnetic retention system shown in FIG. 9. The magnetic retention system 424 illustrated in FIG. 9A is similar in most respects to the magnetic retention system 324. However, it differs from the embodiment shown in FIG. 9A in that the frame 238 of the magnetic retention system 424 has an opening defined therethrough that forms an elongated, rectangular enclosure 240 adapted to receive a short golf pencil 180. The enclosure 240 formed by the frame 238 provides a pocket that readily receives the pencil 180. In the magnetic retention system 424, only a single magnet 36 is necessary since the pencil 180 is so short. The pencil 180 must, however, be equipped with some metal portion, such as a thin iron or steel band 182. The magnet 36 acts through the fabric layer 141 to exert a force of magnetic attraction on the metal band 182 sufficient to hold the pencil 180 seated in the pocket 240.

Figure 11:
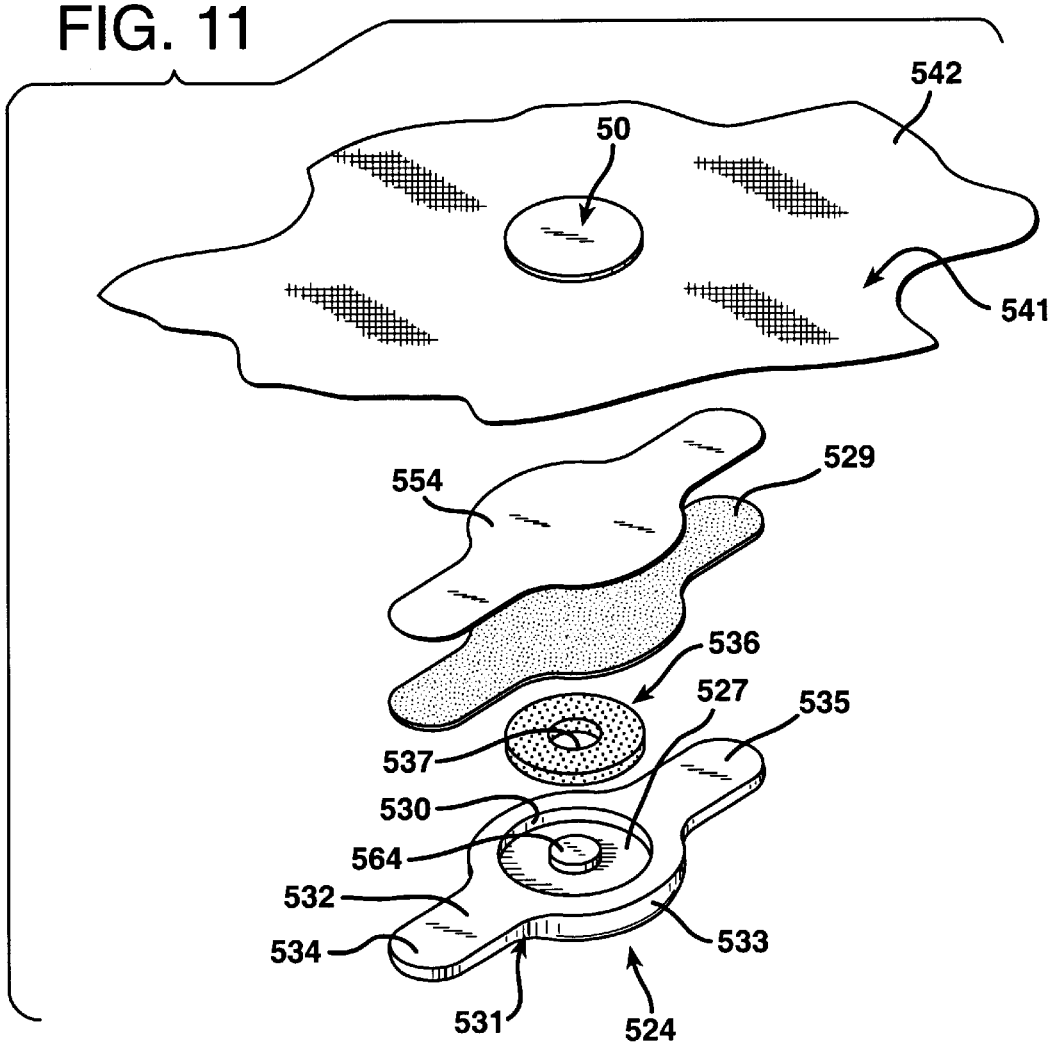
FIG. 11 is an exploded perspective view illustrating one embodiment of an apparatus according to the invention.
Figure 12:
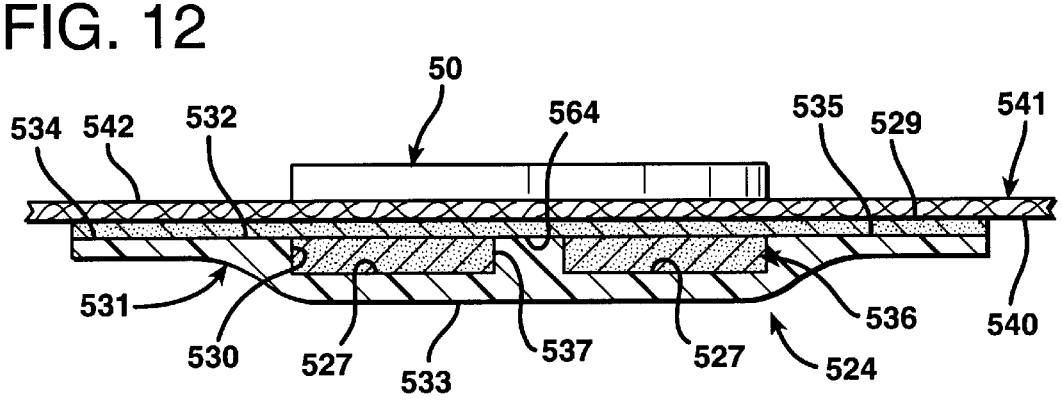
FIG. 12 is a sectional detail illustrating the embodiment of FIG. 11 as applied and used.

FIGS. 11 and 12 illustrate an embodiment of a magnetic retention system indicated generally at 524 which is suitable for attachment to virtually any article of clothing, or any other fabric article utilized as a sporting or recreational accessory. The magnetic retention system 524 includes a shallow tray 526 formed as a molded structure of flexible plastic, such as polyvinyl chloride. The tray 526 is molded to include a flat floor 527 having an annular shape, and short cylindrical walls 530 extending upwardly from the floor 527. At the center of the tray 526 there is a short, upright, disc-shaped mounting post 564 that extends upwardly from the floor 527 the same distance as the walls 530. The tray 526 also includes a rim 531 having an outwardly facing flat annular attachment surface 532 that surrounds the cavity formed within the walls 530 and above the floor 527.

The magnetic retention system 524 also includes a permanent magnet 536 formed as a flat, annular ring with an opening 537 defined therethrough. The ring magnet 536 fits snugly into the cavity formed within the walls 530 and atop the floor 527. The mounting post 564 extends snugly up into the central opening 537 in the ring magnet 536 to form a frictional engagement between the mounting post 564 and the ring magnet 536. The permanent magnet 536 is thereby disposed in the cavity of the tray 526.

The rim 531 includes an enlarged central portion 533 and wings 534 and 535 projecting in opposite directions from the larger, central region 533. The magnetic retention system 524 also includes a layer 529 of adhesive on the attachment surface 532 of the rim 531 of the tray 526. The adhesive layer 529 establishes an adhesive bond with a layer of fabric, such as the fabric layer 541, placed in contact therewith. The adhesive layer 529 forms an adhesive bond both with the attachment surface 532 of the tray rim 531 and also with the undersurface 540 of the fabric layer 541. The undersurface 540 of the fabric layer 541 is typically a concealed surface that lies opposite a visually exposed surface 542 of the fabric layer 541.

The adhesive layer 529 establishes a firm, adhesive bond both with the fabric layer 541 and also with the attachment surface 532 of the rim 531 of the tray 526. To prevent premature contact of the adhesive layer 529 with any surface other than the surface 540 of the fabric layer 541 at a predetermined, desired position of attachment thereon, the adhesive layer 529 is initially covered with a film 554, the undersurface of which is coated with a release agent. The release agent faces the adhesive layer 529 and permits only a light adhesive bond between the film 554 and the adhesive layer 529.

When the magnetic retention system 524 is to be attached to a layer of fabric 541, the release-coated film 554 is stripped from the adhesive layer 529 and the adhesive layer 529 is pressed into contact with the surface 540 of the fabric layer 541 at a desired position of attachment relative thereto. Once the plastic tray 526 with the ring magnet 536 mounted therein has been attached to the fabric layer 541, the magnet 536 exerts a magnetic force of attraction through the structure of the fabric layer 541. This magnetic force of attraction is sufficient to firmly but releasably hold a small ferrous article, such as the iron or steel ball marker 50, in contact with the outer, visually exposed surface 542 of the fabric layer 541.

The magnetic field of the ring magnet 536 easily acts through both the adhesive layer 529 and the structure of the fabric layer 541 to exert a sufficient magnetic force upon the ball marker 50 to hold it firmly in position in coaxial alignment with the ring magnet 536. The permanent ring magnet 536 holds the golf ball marker 50 in contact with the fabric material 541 in registration with and on a side thereof opposite the adhesive layer 529. The golf ball marker 50 is formed of an iron or steel material, or any other material that is attracted by the force of magnetism exerted by the ring magnet 536.

Figure 13:
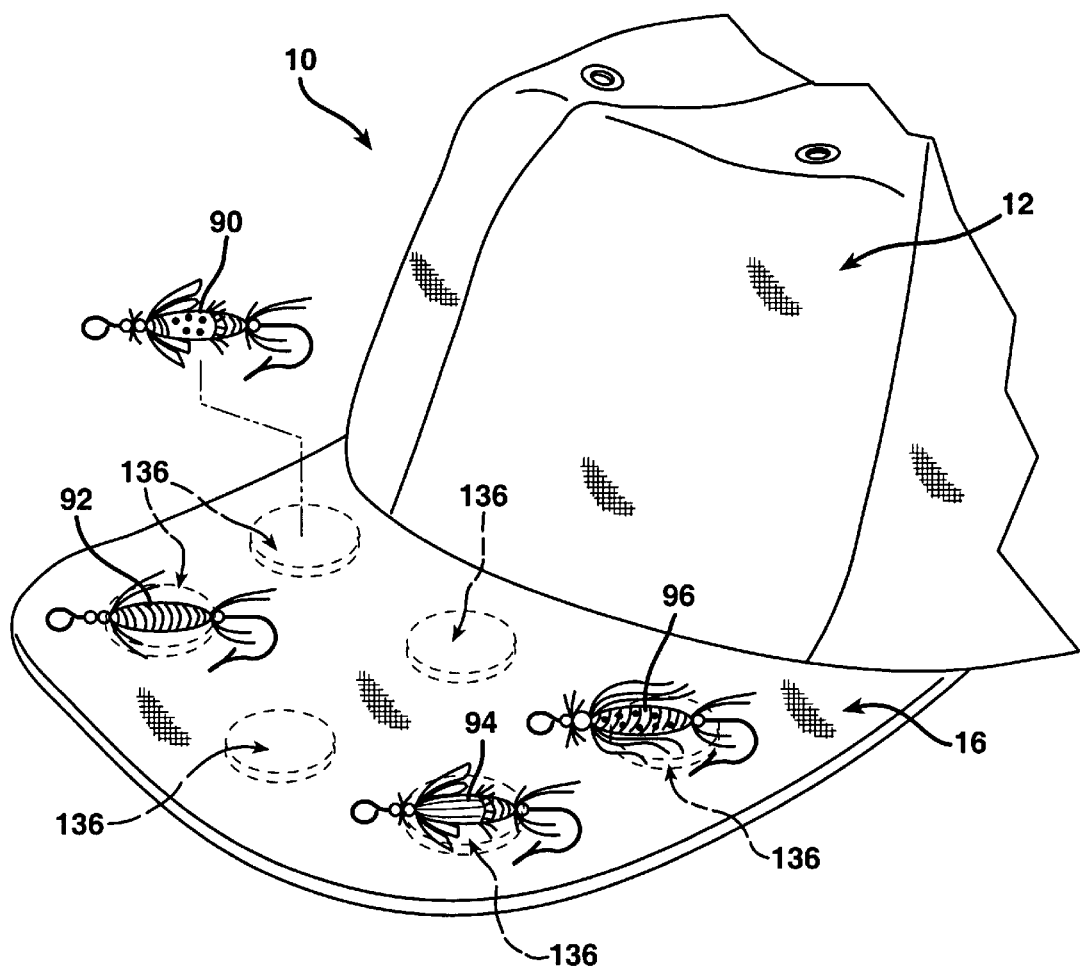
FIG. 13 illustrates an alternative embodiment of the invention as incorporated into a fishing hat.

The use of the system of the invention is not limited to golf accessories. Indeed, it may be utilized with virtually any sporting or recreational activity in which it is desirable for small articles subject to the force of magnetism to be held on articles of clothing or other fabric products. For example, FIG. 18 illustrates the same hat 10 described in conjunction with FIGS. 1 and 2 and having magnets 36 embedded therein as described in conjunction with FIGS. 4 and 5, but utilized in a different environment. Specifically, FIG. 13 illustrates the hat 10 with magnets 36 embedded therein used to hold artificial fishing flies 90, 92, 94, and 96 on the bill 16 of the hat 10. In conventional practice sports men and women who engage in fly casting often hook their favorite artificial flies through the structure of their hats in order to allow the artificial flies to dry and fluff out when not in use. However, by repeatedly hooking and unhooking the artificial lures in the fabric of the hat, the hat rapidly suffers deterioration due to the barbs on the artificial flies. The magnetic retention system of the present invention represents a very useful alternative that avoids the damage to the hat 10. As shown in FIG. 13, the force of magnetic attraction of the magnets 36 embedded in the bill 16 of the hat 10 act upon the iron or steel hooks in the artificial fishing flies 90, 92, 94, and 96. As a consequence, the artificial flies will remain magnetically held upon the bill 16 of the hat 10, by only the force of magnetism and without any damage to the hat 10 since the hooks are not embedded in the fabric structure of the hat.

Numerous other applications of the invention will also become readily apparent to those familiar with the game of golf and other sporting and recreational activities. For example, flexible rubber discs in which magnetized iron or iron oxide particles are embedded, or hard magnetized wafers of rubber in which magnetized iron or iron oxide particles are embedded can be utilized as permanent magnets in place of the iron magnetic discs and rings illustrated. Also, lengths of magnetized wire can be utilized as the appropriate permanent magnets. Accordingly, the scope of the invention should not be construed as limited to the specific embodiments illustrated, as other forms of the invention will become readily apparent in view of the disclosure herein.

I claim:

1. In an article of clothing having at least one layer of fabric having a visually exposed side and an opposite concealed side, the improvement comprising a permanent magnet secured in position to said layer of fabric at a selected, fixed location thereon against said concealed side thereof to exert a magnetic field that acts entirely through said layer of fabric from said selected fixed location with a strength that acts at said visually exposed side of said layer of fabric and a golf accessory formed of a material attracted by magnetism and which is drawn into contact and held by the force of magnetism against said visually exposed side of said layer of fabric when moved into said magnetic field at said visually exposed side of said layer of fabric, and which is completely removable for use from contact with said layer of fabric.

2. An article of clothing according to claim 1 wherein said rim is formed of a flat sheet of flexible stock and said walls of said cavity are defined as the sides of an opening through said flat sheet of stock, and said tray is further comprised of a flat patch having a first face that forms said floor of said tray and which is covered with an adhesive to hold said magnet secured in said tray against said floor, and said patch has a peripheral margin that extends laterally beyond said opening in said sheet of stock and said peripheral margin is captured between said attachment surface of said rim at said fixed location and said visually exposed side of said layer of fabric.

3. An article of clothing according to claim 2 wherein said tray is further comprised of a ball marker retaining ring disposed in contact with said rim of said tray opposite said attachment surface thereof so as to surmount said rim with said patch centered therebeneath to thereby define a laterally constraining enclosure, and further comprising a golf ball marker formed of a material attracted by said permanent magnet and removably positionable atop said magnet and within the lateral confines of said enclosure.

4. An article of clothing according to claim 3 wherein said flat sheet of stock, said retaining ring and said patch are all formed of flexible materials, and further comprising a fastening system for securing said retaining ring to said sheet of flat stock and for securing said rim to said layer of fabric.

5. An article of clothing according to claim 1 further comprising a shallow tray formed of a sheet of flexible material and defining a tray cavity having a floor, walls projecting outwardly from said floor, and a rim extending laterally beyond said walls and having an outwardly facing attachment surface surrounding said cavity and said attachment surface of said rim is secured to said concealed side of said layer of fabric, thereby encapsulating said magnet between said tray and said concealed side of said layer of fabric.

6. An article of clothing according to claim 5 wherein said tray is fabricated from a flexible, plastic material, and is attached to said fabric by a layer of adhesive interposed therebetween.

7. An article of clothing according to claim 6 wherein said magnet is formed in an annular, disc-shaped configuration, and said floor of said tray has an annular shape with a center post centrally located within said tray cavity and extending outward to a level even with said tray walls, and said magnet is frictionally engaged on said center post.

8. An article of clothing according to claim 1 which further comprises a flat stiffening layer having a circular opening defined therethrough and which is located and resides in contact with said concealed side of said at least one layer of fabric and another layer of fabric located on a side of said stiffening layer opposite said at least one fabric layer, thereby forming a cavity for said magnet completely enclosed between said fabric layers and surrounded by the structure of said stiffening layer and said magnet is flat and is disposed in said cavity.

9. An article of clothing according to claim 8 further comprising a radially outwardly projecting rib extending laterally from said magnet and an aligned laterally projecting groove defined in said stiffening material about said opening therein and which receives said rib therein to aid in immobilizing said magnet in said cavity.

10. An article according to claim 8 further comprising a radially projecting rib extending laterally from the inside of said opening in said stiffening layer and an aligned, radially inwardly projecting groove defined in the periphery of said magnet and which receives said rib therein to aid in immobilizing said magnet in said cavity.

11. An article according to claim 1 wherein said magnet is configured as a flat, annular ring.

12. An article according to claim 1 further comprising a flat positioning frame secured to said layer of cloth on said visually exposed surface thereof and having a border surrounding an opening therein which has a shape configured to receive and snugly laterally surround an article attracted by magnetism and positioned so that said opening in said frame defines said fixed location on said layer of fabric.

13. In an article of clothing formed of flexible, fabric material, the improvement comprising:

a shallow tray having a floor, walls projecting outwardly from said floor to define a laterally enclosed cavity, and a rim extending laterally beyond said walls and having an outwardly facing attachment surface surrounding said cavity, and a layer of adhesive interposed between said attachment surface of said rim and one surface of said fabric material, thereby joining said tray to said fabric material with said cavity enclosed therebetween and a permanent magnet disposed in said cavity, whereby said magnet exerts a magnetic force of attraction through said fabric material and beyond so that a magnetic field of attraction exists on the side of said fabric material opposite said side thereof at which said layer of adhesive joins said tray to said fabric material, and a golf accessory formed of a material attracted by magnetism and which is drawn into contact with and removably held against said opposite side of fabric material by the force of magnetism when moved into said magnetic field and which is also completely removable from and usable independently of said fabric material.

14. An article according to claim 13 wherein said shallow tray is formed of a flexible, plastic material.

15. An article according to claim 13 wherein said laterally enclosed cavity has an annular disc-shaped configuration and said tray has a central magnet mounting post that extends from said floor to the level of said attachment surface, and said permanent magnet has an annular disc-shaped configuration and fits snugly into said cavity concentrically about said magnet mounting post.

16. An article according to claim 13 wherein said magnetic accessory is a golf ball marker, whereby said permanent magnet holds said golf ball marker in contact with said fabric material in registration therewith on said visually exposed side thereof.

17. An improvement to an article of golf clothing that includes an exposed fabric layer having opposing concealed and exposed surfaces comprising at least one permanent magnet embedded in said article of golf clothing facing said concealed surface of said fabric layer, whereby the magnetic force of attraction of said magnet acts through said fabric layer to exert a magnetic field at said exposed surface of said fabric layer, and a golf accessory comprised of a ferrous material held to said exposed surface of said fabric layer when moved into said magnetic field and completely separable from said fabric layer by overcoming said magnetic force of attraction.

18. An improved golf accessory according to claim 17 wherein said article of golf clothing is a hat.

19. An improved golf accessory according to claim 18 wherein said exposed fabric layer is a cloth covering and said hat has a bill formed of a stiff, flat, interior core encapsulated within said cloth covering, and said at least one permanent magnet is secured to said interior core beneath said cloth covering.

20. An article of clothing according to claim 1 wherein said golf accessory is formed as a ferrous golf ball marker.

21. An article of clothing according to claim 13 wherein said golf accessory is a golf ball marker comprised of steel.

22. An improved article of golf clothing according to claim 17 wherein said golf accessory is a golf ball marker.

23. In combination:

an article of clothing formed with a layer of fabric having a concealed surface and a visually observable surface, an apparatus for securing a magnet to said clothing to attract a ball marker comprising:

a shallow tray having a floor, walls projecting outwardly from said floor to define a laterally enclosed cavity, and a rim extending laterally beyond said walls and having an outwardly facing attachment surface surrounding said cavity and attached to said concealed surface of said fabric;

a permanent magnetic disposed in said cavity of said tray, whereby said magnet is encapsulated between said tray and said fabric and exerts a magnetic force that acts entirely through said layer of fabric to create a magnetic force at said visually observable surface of said layer of fabric; and a golf accessory formed of a material attracted by magnetism and drawn into contact with said visually observable surface of said layer of fabric by magnetic force of said magnet acting entirely through said layer of fabric, and wherein said golf accessory is completely removable from said layer of fabric by overcoming said magnetic force of said magnet.

24. A combination according to claim 23 wherein said golf accessory is a golf ball marker comprised of steel.

* * * * *